United States Patent [19]
Bills et al.

[11] Patent Number: 5,543,429
[45] Date of Patent: Aug. 6, 1996

[54] ANTIFUNGAL AGENTS

[75] Inventors: Gerald F. Bills, Clark; James E. Curotto, Morgan; Sarah J. Dreikorn, Scotch Plains; Rosalind G. Jenkins, Somerset; Jerrold M. Liesch, Princeton Junction; Sandra A. Morris; John R. Thompson, both of Scotch Plains; Deborah L. Zink, Manalapan, all of N.J.; Richard K. Jansson, Doylestown, Pa.; Angela Basilio, Madrid; Teresa Diez, Madrid; Fernando Pelaez, Madrid; Francisca Vicente, Madrid, all of Spain

[73] Assignee: Merck & Co., Inc., Rahway, N.J.

[21] Appl. No.: 401,385

[22] Filed: Mar. 9, 1995

[51] Int. Cl.$^6$ ............................................. A61K 31/34
[52] U.S. Cl. ............................................. 514/468; 549/298
[58] Field of Search ............................ 514/468; 549/298

*Primary Examiner*—Bernard Dentz
*Assistant Examiner*—Amelia Owens
*Attorney, Agent, or Firm*—Elliott Korsen; Mark R. Daniel

[57] ABSTRACT

There are disclosed novel compounds having the formula

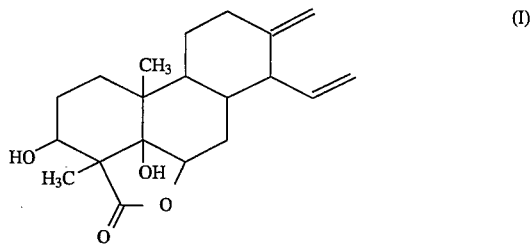

and

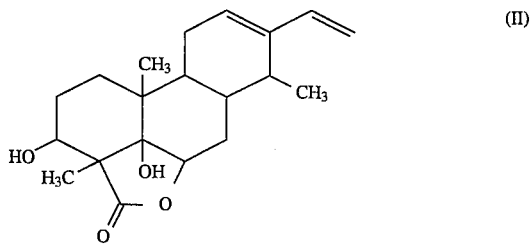

which exhibit antifungal activity.

14 Claims, No Drawings

ANTIFUNGAL AGENTS

BACKGROUND OF THE INVENTION

The present invention relates to novel antifungal compounds, compositions and methods of use. The compounds and compositions exhibit broad spectrum antifungal activity against both human and plant fungal pathogens. Clinical treatment of human fungal infections has relied mainly on two types of antifungal agents. These agents are amphotericin B, which is fungicidal and capable of curing fungal infections at the cost of severe side effects to the patient, and ketoconazole and other azole agents, which exhibit fewer side effects but are only fungistatic.

Currently available crop protection agents may be harmful to human health, susceptible to the development of resistance and limited in their spectrum of activity.

Thus, there is a need for new human and plant antifungal agents.

SUMMARY OF THE INVENTION

The present invention is directed to compounds of the formula (I) and (II):

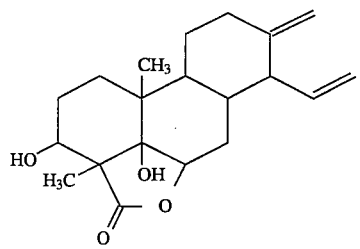

(I)

and

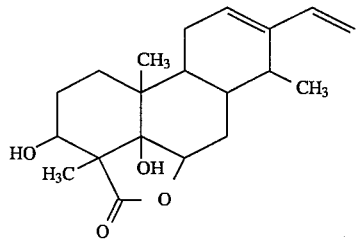

(II)

The compounds have antimicrobial and fungicidal properties and may be useful for controlling systemic and superficial fungal infections in humans with fewer side effects than standard antifungal agents such as amphotericin B or ketoconazole. Additionally, the compounds exhibit activity against plant fungal pathogens and may be useful as a broad spectrum crop antifungal agent.

The compounds are obtained by cultivation of an unidentified sterile fungus MF 6053 in the culture collection of Merck & Co., Inc., Rahway, N.J.

DETAILED DESCRIPTION OF THE INVENTION

The compounds are colorless and characterized by the following spectral properties:

Compound (I)

ULTRAVIOLET SPECTRAL DATA $\lambda_{max}$(MeOH):203 nm ($\epsilon$694)

INFRARED SPECTRAL DATA

Recorded as a thin film on ZnSe,3462,2936,1778,1645, 1425,1178, 1127,921,900,842 $cm^{-1}$

MASS SPECTRAL DATA

Mass spectra were recorded on Jeol SX-102A (electron impact, EI, 90 eV) mass spectrometer. Exact mass measurements were performed at high resolution (HR-EI) using perfluorokerosene (PFK) as the internal standard.

HR EI-MS Found: 332.1996

Calculated for $C_{20}H_{28}O_4$: 332.1987

NMR SPECTRAL DATA

NMR spectra were recorded in $CDCl_3$ at 400 MHz ($^1H$) or 100 MHz ($^{13}C$). Chemical shifts are reported downfield from TMS (tetramethylsilane) and spectra were referenced to solvent peak (7.24 ppm for $^1H$ spectra and 77.0 ppm for $^{13}C$ spectra).

$^{13}C$ NMR Spectra $^{13}C$: d16.1(q),18.6(q),23.2(t),27.1(t),28.9(t),34.5(t), 35.7(d),35.9(t), 40.2(s),45.9(d),54.2(d),58.0(s),69.9(d),74.1 (s),78.9(d),107.0(t), 117.0(t),139.3(d),150.5(s),177.5(s) ppm $^1H$ NMR Spectra $^1H$:δ1.20(m;1H)1.22(s;3H),1.39(m;1H),1.49(m;1H), 1.54(m;1H), 1.54(s;3H),1.64(m; 1H),1.71(m; 1H), 1.72(m;1H),2.01 (m;1H),2.02 (m;1H),2.16(m;1H), 2.25(m;1H),2.27(m;1H),2.43(ddd,13.1, 3.7, 3.7;1H),3.75(br s;1H),3.97(dd, 3.0, 3.0; 1H),4.44(dd,8.7, 3.0; 1H), 4,59(br d;1H),4.68(br d;1H),4.98(dd,17.2, 1.6; 1H),5.15(dd,10.3, 2.1; 1H),5.68(dddd,17.2,10.2,9.8,1.3;1H)ppm Compound (II)

ULTRAVIOLET SPECTRAL DATA $\lambda_{max}$ (MeOH): 230 nm ($\epsilon_{max}$=22,260)

INFRARED SPECTRAL DATA

Recorded as a thin film on ZnSe, 3454,2953,1781,1458, 1410,1378, 1181,1120,1009,900,843,669 $cm^{-1}$

MASS SPECTRAL DATA

Mass spectra were recorded on Jeol SX-102A (electron impact, EI, 90 eV) mass spectrometer. Exact mass measurements were performed at high resolution (HR-EI) using perfluorokerosene (PFK) as the internal standard.

HR EI-MS Found: 332.1981

Calculated for $C_{20}H_{28}O_4$: 332.1987

NMR SPECTRAL DATA

NMR spectra were recorded in $CDCl_3$ at 400 MHz ($^1H$) or 100 MHz ($^{13}C$). Chemical shifts are reported downfield from TMS (tetramethylsilane) and spectra were referenced to solvent peak (7.24 ppm for $^1H$ spectra and 77.0 ppm for $^{13}C$ spectra).

$^{13}C$ NMR Spectra $^{13}C$:δ14.6(q),15.9(q),18.9(q),23.3(t),25.2(t),28.7(t), 29.2(d),31.5(d), 31.7(t),35.1(d),40.1(s),58.2(s),70.0(d), 74.5(s),78.7(d),109.9(t), 127.5(d),138.3(d),141.6(s), 177.7(s)ppm $^1H$ NMR Spectra $^1$H:δ0.94(d,7.1;3H),1.24(s;3H),1.41(ddd,13.5,6.6, 1.7;1H),1.57(s; 3H),1.69(m;1H),1.72(m;1H),1.91(m;1H), 1.92(m;1H),2.03(m;1H), 2.05(m,2H),2.13(dddd,16.0,11.6, 6.7,3.1;1H),2.28(dddd,16.0,8.9,7.5,1.7;1H), 2.43(br dq,7.1, 4.4;1H),3.84(br s;1H),4.09(br s;1H), 4.46(dd,9.0,3.2;1H), 4.90(br d,10.9;1H),5.07(br d,17.6;1H),5.59(br t,4.0;1H), 6.20(dd,17.6,10.9;1H)

The compounds of this invention have antimicrobial properties and are especially useful as antifungal agents against both filamentous fungi and yeasts. They are useful against organisms causing systemic human pathogenic mycotic infections such as Candida albicans, Candida tropicalis, Candida guillermondii, Candida glabrata, Cryptococcus neofromans, Aspergillus fumigatus, Candida pseudotropicalis, Saccharomyces cerevisiae, Aspergillus flavus et al. They are also useful against organisms causing superficial fungal infections such as Trichoderma sp. and Candida sp. These properties may be effectively utilized by administering compositions containing an antifungal amount of Compound I or II to an area, object or subject, on or in which fungi are to be controlled. Thus, compositions containing an antifungally effective amount of Compound I or II and their use for the control of fungi are aspects of the present invention. An especially preferred aspect of the present invention are compositions in a pharmaceutically acceptable carrier and their use for the control of mycotic infections by administering a therapeutically effective amount of one or both of the compounds.

The compounds of this invention also have agricultural antifungal properties. Compounds I and II are especially useful as an antifungal agent against certain Oomycetes on plants, including potato late blight, Phytophthora infestans, and downy mildew of grape, Plasmopara viticola. They are also useful as an antifungal agent for control of conidial Ascomycetes (e.g., grey mold, Botrytis cinerea, early blight, Alternaria solani, and glume blotch, Septoria nodorum) and Basidiomycete fungi (e.g., wheat leaf rust, Puccinia recondita). These properties may be utilized by administering compositions containing an antifungal amount of one or both of the compounds to an area, object or subject, on or in which fungi are to be controlled. When the term control is used, it is intended to imply both prophylactic use and curative use of the compound.

Depending on the circumstances (such as the type of crop where fungi are to be combatted, the environmental conditions, or other factors), the composition of the present invention in addition to the antifungal compounds may also contain other active ingredients such as biocides, pesticides, herbicides, insecticides, nematocides, acaricides or plant nutrients or fertilizers.

The compounds of the present invention are natural products produced from a liquid fermentation of an unidentified sterile fungus MF 6053 in the culture collection of Merck & Co., Inc., Rahway, N.J., which has been deposited under the Budapest Treaty in the culture collection of the American Type Culture Collection on Feb. 14, 1995 at 12301 Parklawn Drive, Rockville, Md. 20852 and assigned accession number ATCC 74331.

The fungus which was isolated from dung of domestic sheep collected near Glen Ellen, Sonoma County, Calif., was grown on a variety of mycological media under different light regimes, and on cellulosic materials such as sterilized leaves and filter paper but in all cases, it failed to sporulate and thus could not be identified.

In agar culture, colonies of the fungus exhibit the following morphology:

Colonies on oatmeal agar (Difco) at 25 C, 12 hr photoperiod attaining 39–43 mm in 21 days, raised, with advancing zone appressed, even, with aerial mycelium floccose to lanose, dull, obscurely zonate, at first white but soon mottled pale gray to dark gray, Dawn Gray, Hathi Gray, Castor Gray (capitalized color names from Ridgway, R. 1912), with reverse dull gray, exudates absent.

Colonies on cornmeal agar (Difco), 12 hr photoperiod attaining 36–38 mm in 21 days, submerged to appressed at the margin, raised towards the center, with scant aerial mycelium, translucent, reverse transluscent, exudates absent.

Colonies on YM agar (Difco) at 25 C, 12 hr photoperiod attaining 35 mm in 21 days, raised, velvety to lanose, radially plicate, with some buckling of medium, obscurely zonate, with margin even and submerged, mostly white, but becoming pale gray, Pale Smoke Gray to gray, Storm Gray, reverse dull cream color to pale brownish yellow, exudates absent. No growth at 37° C. on YM.

Hyphal cells are multinucleate when viewed by flurorescent staining with 4', 6'-diamidino-2-phenyindole (Sneh, Burpee & Ogoshi, 1991). The mycelium is composed of highly branched, simple septate, dematiaceous hyphae characteristic of many ascomycetous fungi (Sneh, B., Burpee, L. & Ogoshi, A. 1991. Identification of Rhizoctonia species. American Phytopathological Society: St. Paul).

Although the invention is discussed principally with respect to the specific strain, it is well known in the art that the properties of microorganisms can be varied naturally and artificially. Thus, all strains of the sterile fungus MF 6053, ATCC 74331 including varieties and mutants, whether obtained by natural selection, produced by the action of mutating agents such as ionizing radiation or ultraviolet irradiation, or by the action of chemical mutagens such as nitrosoguanidine, are contemplated to be within the scope of this invention.

The production of Compounds I and II may be carried out by cultivating the sterile fungus MF 6053, ATCC 74331 in a suitable nutrient medium under conditions described herein until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate Compounds I and II from other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium.

TABLE I

| KF SEED MEDIUM | | Trace Element Mix | |
|---|---|---|---|
| | per liter | | per liter |
| Corn Steep Liquor | 5 g | $FeSO_4.7H_2O$ | 1 g |
| Tomato Paste | 40 g | $MnSO_4.4H_2O$ | 1 g |
| Oat flour | 10 g | $CuCl_2.2H_2O$ | 25 mg |
| Glucose | 10 g | $CaCl_2$ | 100 mg |
| Trace Element Mix | 10 ml | $H_3BO_3$ | 56 mg |
| | | $(NH_4)_6Mo_7O_{24}.4H_2O$ | 19 mg |
| pH = 6.8 | | $ZnSO_4.7H_2O$ | 200 mg |

TABLE 2

PRODUCTION MEDIUM CYS80

| Component | per liter |
|---|---|
| Sucrose | 80 g |
| Corn Meal (yellow) | 50 g |
| Yeast Extract | 1 g |

No pH adjustment

TABLE 3

PRODUCTION MEDIUM F202

| Millet | 15.0 g/flask |
|---|---|
| Base liquid | 15.0 mLs/flask |
| Base Liquid | per liter |
| Sucrose | 33.3 g |
| Alfalfa | 33.3 g |
| Yeast Extract | 33.3 g |
| Sodium tartrate | 6.67 g |
| Corn Oil | 6.67 mL |
| $FeSO_4.7H_2O$ | 0.67 g | no pH adjustment, autoclave 15 minutes (121° C., 15 psi)
add 15.0 mls distilled $H_2O$/flask, autoclave 20 minutes (121° C., 15 psi)

Of the foregoing media, the CYS80 medium, was found to give the best yield of Compounds I and II. In the production of the compounds, generally, the culture is first grown in a seed medium and the culture growth then used to inoculate a production medium. The production medium may be a solid medium or a liquid medium.

The unidentified culture was maintained in sterile soil and stored at 4° C. until ready for use. The seed culture was inoculated by aseptically transferring a small amount of the preserved soil into a 250 ml Erlenmeyer flask containing 50 mls of seed medium of the following composition (in g/liter); corn steep liquor, 5.0; tomato paste, 40.0; oat flour, 10.0; glucose, 10.0; and trace elements solution, 10 mls/liter (consisting of, in g/liter: $FeSO_4.7H_2O,1.0;MnSO_4.4H_2O$, 1.0;$CuCl_2.2H_2O$,0.025; $CaCl_2.2H_2O$,0.1; $H_3BO_3$, 0.056; $(NH_4)_6MoO_{24}.4H_2O$,0.019; $ZnSO_4.7H_2O$,0.2; dissolved in 0.6N HCl ). Seed medium was prepared with distilled water, the pH was adjusted to 6.8 by adding NaOH and the medium dispensed into 250 ml Erlenmeyer flasks and capped with cotton plugs before being autoclaved at 121° C. for 20 minutes. The seed culture was incubated at 25° C. on a gyratory shaker (220 rpm, 5.1 cm throw) for 73 hours prior to the inoculation of fermentation flasks.

The production medium was formulated as follows (in g/liter): sucrose, 80.0; yellow corn meal, 50.0; and yeast extract, 1.0. This medium was prepared using distilled water; 50 mls medium was dispensed into 250 ml Erlenmeyer flasks that were capped with cotton plugs before being autoclaved at 121° C. for 20 minutes. Fermentation flasks were inoculated with 2.0 mls vegetative seed growth and were incubated at 25° C., on a gyratory shaker (220 rpm, 5.1 cm throw) for 13 days. Each fermentation flask was homogenized, extracted with 40.0 mLs of MEK (methyl ethyl ketone), shaken for 30 minutes, pooled and delivered for the isolation of Compounds I and II.

The usefulness of Compounds I and II as antifungal agents, especially as antimycotic agents, may be demonstrated with Compound I or II in a broth microdilution assay for the determination of minimum inhibitory concentration (MIC) and minimum fungicidal concentration (MFC) against fungi. In such assay against a panel of fungi selected for their resistance/susceptibility to known compounds, animal virulence, source and clinical importance, Compounds I or II are found to be effective at concentrations comparable to an established antifungal agent, amphotericin B.

In the microbroth dilution assay, microorganisms were selected by streaking a yeast culture on Sabouraud dextrose agar (SDA) incubating for 24–48 hours at 35°–37° C., thereafter selected 3 to 5 characteristic colonies and transferring to a fresh plate and incubating under similar conditions. From the regrowth, 3 to 5 colonies were selected and suspended in 10 milliliters of YM broth (Difco) and incubated for 4 hours at 35°–37° C. shaking at 225 rpm. The 4 hour broth cultures were adjusted optically to 86% transmission resulting in a concentration of $1-5\times10^6$ cfu/ml which was further diluted 1:100 in YNBD (yeast nitrogen base with 1% dextrose) to obtain a concentration of $1-5\times10^4$ cfu/ml for use as inocula.

The test compounds, Compounds I and II, were dissolved at 512 µg/ml in 10% DMSO and diluted 2X into the first well to achieve a concentration of 256 µg/ml at 5% DMSO in the first well. Compounds are subsequently serially diluted 2X and cell suspension is added to each well resulting in an additional 2X dilution of compound. 75 µl of said solution is delivered to each well in column 1 of a 96-well, U-bottomed microtiter plate. The compounds in column 1 were then serially diluted two-fold to yield concentrations from 128 µg/ml to 0.06 µg/ml.

Amphotericin B, the control compound, was prepared as a stock solution of 512 µg/ml in 10% DMSO and 75 µl of said solution delivered to column 1 of a 96-well, U-bottomed microtiter plate. The compounds in column 1 were then serially diluted two-fold to yield concentrations from 128 µg/ml to 0.6 µg/ml.

The plates containing the diluted compounds were then inoculated with 75 µl/well of the appropriate microorganism and incubated for 48 hours at 35°–37° C. with MIC (minimum inhibitory concentration) determinations carried out after 24 hours of incubation (except Cryptococcus strains which are read at 48 hours) Growth and sterility controls for each organism and sterility checks for the compounds also were carried out.

After recording MICs at 24 hours, the microtiter plates were shaken gently to resuspend the cells. A 1.5 μl sample was transferred from each well of the 96-well microtiter plate to a single reservoir inoculum plate containing SDA. The inoculated SDA and corresponding microtiter plates were incubated for 24 hours at 35°–37° C. For *Cryptococus neoformans*, SDA plates were inoculated at 48 hours after recording MICs and incubated 48 hours before reading the MFC. MFC is the lowest concentration of compound at which either no growth or growth of ≦4 colonies occur.

Compounds I and II were compared with established agricultural antifungal agents, metalaxyl or propiconazole. Test plants were sprayed to runoff with different concentrations of the test materials and then inoculated after spray material had dried with each of the seven pathogens. After inoculation, plants were placed in one of three controlled-environment rooms set at either 18° C., 22° C. or 24° C. Non-treated plants inoculated with each disease were used as control. Plants were rated visually for percent control of each disease. Plants inoculated with *P. infestans*, *A. solani*

| | Minimum Fungicidal Concentration (MFC) Minimum Inhibitory Concentration (MIC) (ug/ml) | | | | | | | | |
|---|---|---|---|---|---|---|---|---|---|
| | Candida | | | | | | | | |
| | albicans MY1055 | glabrata MY1381 | parapsilosis MY1010 | pseudotropicalis MY2099 | tropicalis MY1124 | albicans CLY539 | albicans CA2 | tropicalis MY1012 | guillermondii MY1019 |
| Compound I | | | | | | | | | |
| MIC | 2 | 8 | 8 | 4 | 8 | 4 | 8 | 2 | 8 |
| MFC | 4 | 8 | 32 | 4 | 16 | 2 | 8 | 2 | 16 |
| Compound II | | | | | | | | | |
| MIC | 2 | 4 | 8 | 1 | 4 | 2 | 32 | 2 | 8 |
| MFC | 4 | 4 | 8 | 2 | 8 | 2 | 4 | 2 | 16 |
| Control* | | | | | | | | | |
| MIC | 1 | 2 | 1 | 2 | 2 | 1 | 1 | 16 | 1 |
| MFC | 1 | 2 | 1 | 2 | 2 | 2 | 1 | 16 | 2 |

*Amphotericin B

| | Minimum Fungicidal Concentration (MFC) Minimum Inhibitory Concentration (MIC) (ug/ml) | | | | | |
|---|---|---|---|---|---|---|
| | Cryptococcus | | Saccharomyces | | Aspergillus | |
| | neoformans MY2061 | neoformans MY2062 | cerevisiae MY2140 | cerevisiae MY2141 | fumigatus MY4839 | fumigatus MY5668 |
| Compound I | | | | | | |
| MIC | 0.5 | 0.25 | 2 | 1 | 4 | 8 |
| MFC | 0.25 | 0.25 | 8 | 8 | | |
| Compound II | | | | | | |
| MIC | 2 | 1 | 1 | 0.5 | 2 | 1 |
| MFC | 1 | 1 | 2 | 1 | | |
| Control* | | | | | | |
| MIC | | 1 | 1 | 1 | 2 | 2 |
| MFC | | — | 1 | 1 | — | — |

*Amphotericin B

Compounds I and II are also useful as broad spectrum antifungal agents for agricultural use as shown in an in vivo assay using various phytopathogens. In the assay, a panel of seven pathogens (late blight, *Phytophthora infestans*; on tomato; early blight, *Alternaria solani*; on tomato; downy mildew, *Plasmopara viticola*; on grape; grey mold, *Botrytis cinerea*; on pepper; glume blotch, *Septoria nodorum*; on wheat; wheat leaf rust, *Puccinia recondita*; on wheat; and powdery mildew of wheat, *Erysiphe graminis*) were challenged with different concentrations of the crude broth and with different doses of Compounds I and II in a protectant assay.

and *B. cinerea* were evaluated after four days; those inoculated with *S. nodorum* after 10 days; those with *P. viticola* after 12 days; and plants inoculated with *P. recondita* and *E. graminis* were evaluated after 10–14 days.

Compound I was efficacious at controlling *P. viticola* and *B. cinerea* on plants and resulted in up to 80% control of these diseases when treated with a concentration of 200 ppm. Compound II was very efficacious at controlling six of the phytopathogens. In a miniature plant assay, this compound resulted in 80–95% control of *P. infestans*, *A. solani*, *P. viticola* and *B. cinerea*. In a scaled up, high spray volume assay, Compound II resulted in 100% control of *P. viticola*, *B. cinerea* and *P. recondita*, and 60% control of *S. nodorum* when treated with a concentration of 100 ppm. At 11 ppm, the compound resulted in 50–85% control of *P. viticola* and *B. cinerea* in a protectant assay.

Compounds I and II are also useful for inhibiting the growth of filamentous fungi. Such use may be illustrated in the following tests with *Aspergillus flavus*, *Fusarium oxysporum*, *Ustilago zeae* and the like.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

The samples to be tested for production of antifungal agent are applied directly to the agar plates as methanol solutions. When the sample to be tested is crude broth, it may be centrifuged prior to application. The assay plates are then incubated at either 28° C. or 37° C. for 24 hours. Following incubation, the inhibition zones are measured. Growths are also noted as to appearance. Compounds I and II are seen to effectively inhibit growth of the fungal organisms.

The following example illustrates the invention but is not to be construed as limiting the invention disclosed herein.

EXAMPLE I

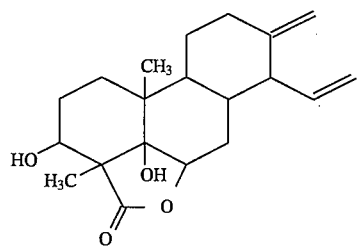

(I)

and

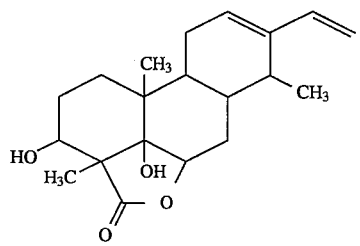

(II)

A culture of the fungus was received as a MEK-extracted whole broth sample. The mixture was filtered in order to remove the mycelia and the organic and aqueous layers were separated. The MEK extract of the 1.5 liters of the fungus culture (1500 ml wbe; 6.7 g) was dried under vacuum and partitioned between 0.1%(v/v) aqueous TFA (350 ml) and CHCl$_3$ (450 ml). The CHCl$_3$ layer was dried under vacuum and a portion of this (representing 700 ml wbe of the original culture; 2.7 g) was chromatographed on silica [EM Merck silica gel 60, 230–400 mesh] using 10% steps of EtOAc in hexane. The bioactive fractions (40–60% EtOAc in hexane) were combined, analysed by HPLC [Zorbax-RXC8 column: 4.6×250 mm; 60% acetonitrile/40% H$_2$O, containing 0.1% (v/v) TFA; 40° C., 1 ml/min] and found to consist of an 80% pure 2:1 mixture of Compound II and Compound I respectively (1.6 g total). A 420 mg sample of this mixture was further purified using preparative scale reversed phase HPLC [room temperature; 80 ml/min; 60% acetonitrile/40% H$_2$O, containing 0.1% TFA]. This final purification step resulted in the production of 70 mg of Compound I and 158 mg of Compound II.

Compounds I and II had the spectral properties previously described.

The following examples illustrate representative compositions containing Compound I or II.

EXAMPLE A 1000 compressed tablets each containing 500 milligrams of Compound I or II are prepared from the following formulation:

|  | Grams |
| --- | --- |
| Compound I or II | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 milligrams of Compound I or II are prepared from the following formulation:

| Compound I or II | 500 |
| --- | --- |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 milliliters of an injectible solution are prepared by conventional procedures from the following formulation:

| Dextrose | 12.5 grams |
| --- | --- |
| Water | 250 milliliters |
| Compound I or II | 400 milligrams |

The ingredients are blended and thereafter sterilized for use.

EXAMPLE D

An ointment suitable for topical application may be prepared by intimately dispersing 13 mg of Compound I or II in 1 g of commercially available polyethylene/hydrocarbon gel.

EXAMPLE E

An aerosol composition may be prepared having the following formulation (per canister):

| Compound I or II | 24 mg |
|---|---|
| Lecithin NF, liquid concentrate | 1.2 mg |
| Trichlorofluoromethane | 4.025 g |
| Dichlorodefluoromethane | 12.15 g |

What is claimed is:

1. A substantially pure compound having the structure:

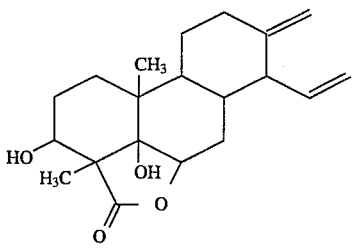

(I)

2. A substantially pure compound having the structure:

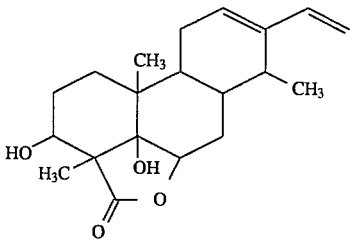

(II)

3. An antifungal composition comprising an antifungal amount of the compound of claim 1 in admixture with a biologically inert carrier or diluent.

4. A composition according to claim 3 wherein the carrier is a pharmaceutically acceptable carrier.

5. A method for controlling fungal growth which comprises administering to the site where growth is to be controlled, an effective amount of the compound of claim 1.

6. A method for combatting fungal infections in mammals which comprises administering to a region of the animal afflicted with said fungi a therapeutically effective amount of the compound of claim 1.

7. A method of combatting fungi in plants which comprises administering to a plant region afflicted with said fungi an effective amount of the compound of claim 1.

8. A method for treating agricultural fungal infections which comprises administering to the site where growth is to be treated an effective amount of the compound of claim 1.

9. An antifungal composition comprising an antifungal amount of the compound of claim 2 in admixture with a biologically inert carrier or diluent.

10. A composition according to claim 9 in which the carrier is a pharmaceutically acceptable carrier.

11. A method for controlling fungal growth which comprises administering to the site where growth is to be controlled, an antifungally effective amount of a compound of claim 2.

12. A method for combatting fungi infections in mammals which comprises administering to a region of the animal afflicted with said fungi a therapeutically effective amount of the compound of claim 2.

13. A method of combatting fungi in plants which comprises administering to a plant region afflicted with said fungi an effective amount of the compound of claim 2.

14. A method for treating agricultural fungal infections which comprises administering to the site where growth is to be treated an effective amount of the compound of claim 2.

* * * * *